(12) United States Patent
Ohkouchi et al.

(10) Patent No.: US 7,976,853 B2
(45) Date of Patent: Jul. 12, 2011

(54) PROCESS FOR PRODUCING COATED PREPARATION

(75) Inventors: Kazuhiro Ohkouchi, Osaka (JP); Masahiko Koike, West Lafayette, IN (US); Hiroyoshi Koyama, Osaka (JP); Naoru Hamaguchi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 926 days.

(21) Appl. No.: 10/542,997

(22) PCT Filed: Jan. 28, 2004

(86) PCT No.: PCT/JP2004/000754
§ 371 (c)(1),
(2), (4) Date: Jul. 21, 2005

(87) PCT Pub. No.: WO2004/067001
PCT Pub. Date: Aug. 12, 2004

(65) Prior Publication Data
US 2006/0141128 A1    Jun. 29, 2006

(30) Foreign Application Priority Data

Jan. 29, 2003 (JP) ................. 2003-020925
Jul. 18, 2003 (JP) ................. 2003-276894
Jan. 6, 2004 (JP) ................. 2004-001128

(51) Int. Cl.
*A61K 9/20* (2006.01)
(52) U.S. Cl. ........................... 424/400
(58) Field of Classification Search ................. None
See application file for complete search history.

(56) References Cited

U.S. PATENT DOCUMENTS

| | | | |
|---|---|---|---|
| 4,892,741 A | 1/1990 | Ohm et al. | |
| 6,153,632 A | 11/2000 | Rieveley | |
| 6,168,806 B1 | 1/2001 | Lee et al. | |
| 6,291,495 B1 | 9/2001 | Rieveley | |
| 6,403,121 B1 | 6/2002 | Adjei et al. | |
| 6,524,621 B2 | 2/2003 | Adjei et al. | |
| 6,692,769 B1 | 2/2004 | Ishibashi et al. | |
| 2002/0004515 A1 | 1/2002 | Smith | |
| 2003/0060488 A1* | 3/2003 | Sugiyama et al. | 514/340 |
| 2003/0187074 A1 | 10/2003 | Hussain et al. | |
| 2004/0086562 A1 | 5/2004 | Shanghvi et al. | |
| 2004/0092480 A1* | 5/2004 | Fujinaga et al. | 514/57 |
| 2004/0106660 A1 | 6/2004 | Kositprapa et al. | |
| 2004/0161462 A1 | 8/2004 | Kositprapa et al. | |

FOREIGN PATENT DOCUMENTS

| | | |
|---|---|---|
| EP | 0616841 A1 * | 9/1994 |
| EP | 0 749 751 | 12/1996 |
| EP | 1 552 832 | 7/2005 |
| EP | 1 561 472 | 8/2005 |
| JP | 51079716 | 12/1974 |
| JP | 2001342185 | * 12/2001 |
| WO | WO 95/07694 | 3/1995 |
| WO | WO 96/36338 | 11/1996 |
| WO | WO 98/53803 | 12/1998 |
| WO | WO 98/57634 | 12/1998 |
| WO | WO 99/47128 | 9/1999 |
| WO | WO 00/16776 | 3/2000 |
| WO | WO 00/24423 | 5/2000 |
| WO | WO 00/28989 | 5/2000 |
| WO | WO 00/28990 | 5/2000 |
| WO | WO 01/35940 | 5/2001 |
| WO | WO 01/35941 | 5/2001 |
| WO | WO 01/37808 | 5/2001 |
| WO | WO 01/82873 | 11/2001 |
| WO | WO 01/82875 | 11/2001 |
| WO | WO 02/04024 | 1/2002 |
| WO | WO 03/005995 | 1/2003 |
| WO | WO 03/105809 | 12/2003 |
| WO | WO 2004/006921 | 1/2004 |
| WO | WO 2004/026241 | 4/2004 |
| WO | WO 2004/030700 | 4/2004 |
| WO | WO 2004/045608 | 6/2004 |
| WO | WO 2004/069229 | 8/2004 |

OTHER PUBLICATIONS

Office Action of Jul. 24, 2009, in corresponding Colombian Patent Application 05084850, 5 pages.

* cited by examiner

*Primary Examiner* — Robert A Wax
*Assistant Examiner* — Bethany Barham
(74) *Attorney, Agent, or Firm* — Foley & Lardner LLP

(57) ABSTRACT

The present invention provides a production method of a preparation coated with pioglitazone hydrochloride, which is useful as a therapeutic agent for diabetes and the like, and which is superior in the characteristics of the preparation such as dissolution property of pioglitazone hydrochloride.

10 Claims, No Drawings

PROCESS FOR PRODUCING COATED PREPARATION

TECHNICAL FIELD

The present invention relates to a production method of a preparation coated with pioglitazone hydrochloride, which is useful as a therapeutic agent for diabetes and the like.

BACKGROUND ART

There are the following reports on pharmaceutical compositions containing an insulin sensitizer such as a thiazolidinedione compound and the like and a biguanide.
1) A pharmaceutical agent, which contains an insulin sensitizer in combination with at least one member from an α-glucosidase inhibitor, an aldose reductase inhibitor, a biguanide, a statin compound, a squalene synthesis inhibitor, a fibrate compound, an LDL catabolism enhancer and an angiotensin converting enzyme inhibitor, is reported (see, EP-749751 A).
2) A pharmaceutical composition, which contains an insulin sensitizer, a biguanide antihyperglycaemic agent and a pharmaceutically acceptable carrier, is reported (see, WO98/57634).
3) A pharmaceutical composition, which contains thiazolidinedione, metformin hydrochloride and a pharmaceutically acceptable carrier, wherein thiazolidinedione is formulated on the surface of metformin hydrochloride, is reported (see, WO01/35940).
4) A pharmaceutical composition, which contains thiazolidinedione, metformin hydrochloride and a pharmaceutically acceptable carrier, wherein thiazolidinedione and metformin hydrochloride are respectively dispersed in pharmaceutically acceptable carriers of their own (see, WO01/35941).
5) A core formulation, which comprises (a) a first layer containing pioglitazone hydrochloride or a pharmaceutically acceptable salt thereof as an active ingredient, and (b) a core containing a biguanide as an active ingredient, wherein at least a part of the core is enclosed by said first layer, is reported (see, WO01/82875).
6) A core formulation, which comprises a first layer containing pioglitazone hydrochloride, which covers at least a part of a core containing a biguanide, wherein one or both of the core and the first layer is/are dispersed in a modulating release agent such as polysaccharides and the like, is reported (see, U.S. Pat. No. 6,403,121).

DISCLOSURE OF THE INVENTION

The present invention aims to provide a production method of a preparation coated with pioglitazone hydrochloride, which is useful as a therapeutic agent for diabetes and the like and superior in preservation stability and the characteristics of the preparation such as dissolution property of pioglitazone hydrochloride.

The present inventors have found, in producing a preparation coated with pioglitazone hydrochloride, that a coated preparation that shows superior dissolution property (particularly, dissolution property within 15 min from the start of dissolution test) of pioglitazone hydrochloride can be obtained by coating with an aqueous dispersion of pioglitazone hydrochloride comprising a coating material having a low viscosity. The present inventors have further studied based on this finding and completed the present invention.

Accordingly, the present invention relates to
1) a production method of a coated preparation, which comprises coating with an aqueous dispersion of pioglitazone hydrochloride comprising a coating material having a low viscosity;
2) a coated preparation obtained according to the production method of the aforementioned 1);
3) the production method of the aforementioned 1), wherein the coating material having a low viscosity in its 5% aqueous solution shows a viscosity of not more than 35 mPa·s at 20° C.;
4) the production method of the aforementioned 1), wherein the coating material having a low viscosity is hydroxypropyl cellulose SL, hydroxypropyl cellulose SSL or polyvinyl alcohol-polyethylene glycol graft copolymer;
5) the production method of the aforementioned 1), wherein a core comprising an active ingredient is coated with an aqueous dispersion of pioglitazone hydrochloride comprising a coating material having a low viscosity;
6) the production method of the aforementioned 5), wherein the active ingredient is a therapeutic agent for diabetes;
7) the production method of the aforementioned 6), wherein the therapeutic agent for diabetes is a biguanide;
8) the production method of the aforementioned 7), wherein the biguanide is metformin hydrochloride;
9) the production method of the aforementioned 5), wherein the active ingredient is a therapeutic agent for hyperlipidemia;
10) the production method of the aforementioned 9), wherein the therapeutic agent for hyperlipidemia is an HMG-CoA reductase inhibitor;
11) a method for improving dissolution of pioglitazone hydrochloride from a preparation coated with pioglitazone hydrochloride, which comprises, when producing said preparation, coating with an aqueous dispersion of pioglitazone hydrochloride comprising a coating material having a low viscosity;
12) a coated preparation obtained according to the production method of the aforementioned 1), which releases not less than 50% of pioglitazone hydrochloride in 15 minutes in a dissolution test by a rotating basket method using a hydrochloric acid-potassium chloride buffer (pH 2.0) as a test solution at 37° C., 100 rpm;
13) a coated preparation obtained according to the production method of the aforementioned 1), which releases not less than 50% of pioglitazone hydrochloride in 15 minutes in a dissolution test by a paddle method using a hydrochloric acid-potassium chloride buffer (pH 2.0) as a test solution at 37° C., 50 rpm; and the like.

The average particle size of pioglitazone hydrochloride used in the present invention is preferably 0.5-500 μm, more preferably 1-150 μm.

The aqueous dispersion to be used in the present invention may be an aqueous solution or an aqueous suspension.

The concentration of pioglitazone hydrochloride in an aqueous dispersion is, for example, 1-25% (W/W), preferably 1-15% (W/W). A concentration of these ranges is preferable from the aspects of coating workability, content uniformity of pioglitazone hydrochloride in the obtained coated preparation and the like.

An "aqueous dispersion of pioglitazone hydrochloride" (hereinafter sometimes to be abbreviated as a dispersion of the present invention) contains a coating material having a low viscosity.

As used herein, by the coating material having a low viscosity is meant, for example, a coating material whose 5% (W/V) aqueous solution has a viscosity of not more than 35 mPa·s (preferably not more than 30 mPa·s, more preferably not more than 25 mPa·s) at 20° C. The viscosity of the coating material may vary when concentration of the coating material in an aqueous solution, measurement conditions such as measurement temperature and the like are different. When the measurement conditions are different, all coating materials having a viscosity value within the aforementioned viscosity range on conversion to the viscosity of a 5% (W/V) aqueous solution at 20° C. are encompassed in the "coating material having a low viscosity" of the present invention.

As the "coating material having a low viscosity", for example, hydroxypropyl cellulose (Grade:SL, SSL (trademark); Nippon Soda Co., Ltd.); hydroxypropyl methylcellulose (Grade:MW, E, EW (trademark); Shin-Etsu Chemical Co., Ltd.)(Grade:E-3 (trademark); Nippon Soda Co., Ltd.); a premix (Grade: SSM (trademark), Nippon Soda Co., Ltd.) of hydroxypropyl cellulose (grade:SSL, Nippon Soda Co., Ltd.) and hydroxypropyl methylcellulose (Grade:E-3); Polyvinyl alcohol-polyethylene glycol graft copolymer [Kollicoat IR (trademark), BASF, Germany] and the like can be mentioned.

The above-mentioned coating material may be a mixture of two or more kinds thereof in an appropriate ratio. When a coating material mixture obtained by combining one or more kinds selected from the above-mentioned coating materials and one or more kinds of coating materials having high viscosity at an appropriate ratio is a "coating material whose 5% (W/V) aqueous solution has a viscosity of not more than 35 mPa·s at 20° C.", this mixture can be used as "a coating material having a low viscosity" of the present invention. As used herein, by the "coating material having high viscosity" is meant, for example, a coating material whose 5% (W/V) aqueous solution has a viscosity of more than 35 mPa·s at 20° C. Specific examples thereof include hydroxypropyl cellulose (Grade: L (trademark); Nippon Soda Co., Ltd.) (Grade: Klucel EF, Klucel LF (trademark); Aqualon (USA)); hydroxypropyl methylcellulose (Grade: R (trademark); Shin-Etsu Chemical Co., Ltd.); and the like.

A coating material having a low viscosity preferably includes hydroxypropyl cellulose SL (viscosity of 5% aqueous solution at 20° C.: about 24 mPa·s; and/or viscosity of 2% aqueous solution at 20° C.: 3.0-5.9 mPa·s), hydroxypropyl cellulose SSL (viscosity of 5% aqueous solution at 20° C.: about 8 mPa·s; and/or viscosity of 2% aqueous solution at 20° C.: 2.0-2.9 mPa·s), Polyvinyl alcohol-polyethylene glycol graft copolymer [Kollicoat IR (trademark), BASF, Germany] (viscosity of 5% aqueous solution at 20° C.: about 18 mPa·s) and the like.

A coating material having a low viscosity may be dissolved or suspended in the dispersion of the present invention. For efficient production of a coated preparation superior in content uniformity of pioglitazone hydrochloride and strength of the preparation, the coating material is preferably dissolved in the dispersion of the present invention.

The dispersion of the present invention may further contain a coating additive. As the coating additive, for example, shading agents and/or coloring agents such as titanium oxide, talc, ferric oxide and the like; plasticizers such as polyethylene glycol, triethyl citrate, castor oil, polysorbates and the like; organic acids such as citric acid, tartaric acid, malic acid, ascorbic acid and the like; lactose, D-mannitol, low-substituted hydroxypropyl cellulose, carmellose calcium, crospovidone and the like can be mentioned.

When the coating additive is not water soluble, the average particle size thereof is preferably not more than 500 μm, more preferably not more than 150 μm, particularly preferably not more than 75 μm. When a coating additive having such average particle size is used, a coated preparation superior in content uniformity of pioglitazone hydrochloride and strength of the preparation can be obtained efficiently.

The concentration of the coating material having a low viscosity in the dispersion of the present invention is, for example, 1-30% (W/W), preferably 1-25% (W/W), more preferable 2-25% (W/W). Concentrations in these ranges are preferable in view of coating workability, content uniformity of pioglitazone hydrochloride in the obtained coated preparation, and the like.

The concentration of the coating additive in the dispersion of the present invention is, for example, 0.2-35% (W/W), preferably 0.2-30% (W/W), more preferable 0.5-15% (W/W). Concentrations in these ranges are preferable in view of coating workability, content uniformity of pioglitazone hydrochloride in the obtained coated preparation, and the like.

As the core to be coated with an aqueous dispersion of pioglitazone hydrochloride comprising a coating material having a low viscosity (hereinafter sometimes to be abbreviated as a core of the present invention), for example, solid preparations such as tablet, capsule, granule, powder, troche and the like can be mentioned. The solid preparation may be a controlled release preparation such as immediate release preparation, release sustaining preparation (sustained release preparation) and the like. The solid preparation may contain a conventional additive in the field of pharmaceutical preparation and can be also produced according to a known method. As the additive, for example, excipient, disintegrant, binder, lubricant, coloring agent, pH regulator, surfactant, release-sustaining agent, stabilizer, sour agent, flavor, glidant and the like can be mentioned. These additives are used in an amount conventionally employed in the field of pharmaceutical preparation.

As the excipient, for example, starches such as corn starch, potato starch, wheat starch, rice starch, partly pregelatinized starch, pregelatinized starch, porous starch and the like; sugars and sugar alcohols such as lactose, fructose, glucose, D-mannitol, sorbitol and the like; anhydrous calcium phosphate, crystalline cellulose, precipitated calcium carbonate, calcium silicate and the like can be mentioned.

As the disintegrant, for example, carboxymethyl cellulose, calcium carboxymethyl cellulose, sodium carboxymethyl starch, croscarmellose sodium, crospovidone, low-substituted hydroxypropyl cellulose, hydroxypropyl starch and the like are used. The amount of the disintegrant to be used is preferably 0.5-25 parts by weight, more preferably 1-15 parts by weight, per 100 parts by weight of the solid preparation.

As the binder, for example, crystalline cellulose, hydroxypropyl cellulose, hydroxypropylmethyl cellulose, polyvinylpyrrolidone, gum arabic powder and the like can be mentioned. The amount of the binder to be used is preferably 0.1-50 parts by weight, more preferably 0.5-40 parts by weight, per 100 parts by weight of the solid preparation.

Preferable examples of the lubricant include magnesium stearate, calcium stearate, talc, sucrose esters of fatty acids, sodium stearyl fumarate and the like.

As the coloring agent, for example, food colors such as Food Yellow No. 5, Food Red No. 2, Food Blue No. 2 and the like, food lake colors, ferric oxide and the like can be mentioned.

As the pH regulator, citrate, phosphate, carbonate, tartrate, fumarate, acetate, amino acid salt and the like can be mentioned.

As the surfactant, sodium lauryl sulfate, polysorbate 80, polyoxyethylene (160) polyoxypropylene (30) glycol and the like can be mentioned.

As the release-sustaining agent, for example, cellulose polymers such as hydroxypropyl cellulose, hydroxypropylmethyl cellulose (preferably hydroxypropylmethyl cellulose 2910, hydroxypropylmethyl cellulose 2208 and the like), cellulose acetate (preferably cellulose acetate having an acetyl content of 39.3-40%), cellulose diacetate, cellulose triacetate, cellulose acetate propionate, ethyl cellulose, sodium carboxymethyl cellulose, crystalline cellulose sodium carboxymethyl cellulose and the like; sodium alginate, carboxyvinyl polymer; acrylic acid polymers such as aminoalkylmethacrylate copolymer RS [Eudragit RS (trademark), Rohm Pharma], ethyl acrylate-methyl methacrylate copolymer suspension [Eudragit NE (trademark), Rohm Pharma] and the like; and the like can be mentioned. The release-sustaining agent may contain, for example, flux enhancers (e.g., sodium chloride, potassium chloride, sucrose, sorbitol, D-mannitol, polyethylene glycol (preferably polyethylene glycol 400 and the like), propylene glycol, hydroxypropyl cellulose, hydroxypropylmethyl cellulose, hydroxypropylmethyl cellulose phthalate, cellulose acetate phthalate, polyvinyl alcohol, methacrylic acid polymer), plasticizers (e.g., triacetin, acetylated monoglyceride, grape seed oil, olive oil, sesame oil, acetyltributyl citrate, acetyltriethyl citrate, glycerin sorbitol, diethyl oxalate, diethyl maleate, diethyl fumarate, dibutyl succinate, diethyl malonate, dioctyl phthalate, dibutyl sebacate, triethyl citrate, tributyl citrate, glycerol tributyrate) and the like. Preferable examples of the release-sustaining agent include (1) a semipermeable membrane coating containing cellulose acetate (preferably cellulose acetate having an acetyl content of 39.3-40%), polyethylene glycol (preferably polyethylene glycol 400 and the like) and triacetin; (2) a release-sustaining composition containing sodium carboxymethyl cellulose, hydroxypropylmethyl cellulose 2910, hydroxypropylmethyl cellulose 2208 and microcrystalline cellulose; and the like.

As the stabilizer, for example, tocopherol, tetrasodium edetate, nicotinamide, cyclodextrins and the like can be mentioned.

As the sour agent, for example, ascorbic acid, citric acid, tartaric acid, malic acid and the like can be mentioned.

As the flavor, for example, menthol, peppermint oil, lemon oil, vanillin and the like can be mentioned.

As the glidant, for example, light anhydrous silicic acid, hydrated silicon dioxide and the like can be mentioned.

The above-mentioned additives may be used in a mixture of two or more kinds thereof in an appropriate ratio.

The core of the present invention preferably contains an active ingredient. As used herein, as the active ingredient, therapeutic agents for diabetes, therapeutic agents for diabetic complications, therapeutic agents for hyperlipidemia, antihypertensive agents, antiobesity agents, diuretics, antithrombotic agents and the like can be mentioned. These active ingredients may be a low-molecular-weight compound, a high-molecular-weight protein, polypeptide or antibody, a vaccine or the like. The active ingredient may be a mixture of two or more kinds of components in an appropriate ratio.

Use of a core containing an active ingredient as the core of the present invention in this way affords superior effects such as 1) enhancing the action of pioglitazone hydrochloride or an active ingredient (synergistic effect on the action of pharmaceutical agent), 2) reducing the dose of pioglitazone hydrochloride or an active ingredient (effect of reducing the dose of pharmaceutical agent as compared to a single drug administration), 3) reducing the secondary action (e.g., body weight gain action, ketosis, acidosis) of pioglitazone hydrochloride or an active ingredient, and the like.

Examples of the therapeutic agents for diabetes include insulin preparations (e.g., animal insulin preparations extracted from the pancreas of cattle, swine; human insulin preparations synthesized by genetic engineering techniques using *Escherichia coli* or yeast; zinc insulin; protamine zinc insulin; fragments or derivatives of insulin (e.g., INS-1 etc.) and the like), insulin sensitizers (e.g., pioglitazone or its salt (preferable hydrochloride), rosiglitazone or its salt (preferable maleate), GI-262570, reglixane (JTT-501), netoglitazone (MCC-555), YM-440, KRP-297, CS-011, FK-614, compounds described in WO99/58510 (e.g., (E)-4-[4-(5-methyl-2-phenyl-4-oxazolylmethoxy)benzyloxyimino]-4-phenylbutyric acid), ragaglitazar (NN-622), tesaglitazar (AZ-242), BMS-298585, ONO-5816, LM-4156, BM-13-1258, MBX-102, GW-1536, LY-519818 etc.), α-glucosidase inhibitors (e.g., voglibose, acarbose, miglitol, emiglitate etc.), biguanides (e.g., phenformin, metformin, buformin, or a salt thereof (e.g., hydrochloride, fumarate, succinate) etc.), insulin secretagogues [sulfonylureas (e.g., tolbutamide, glibenclamide, gliclazide, chlorpropamide, tolazamide, acetohexamide, glyclopyramide, glimepiride, glipizide, glybuzole etc.), repaglinide, nateglinide, mitiglinide or calcium salt hydrate thereof, GLP-1 etc.], dipeptidylpeptidase IV inhibitors (e.g., NVP-DPP-278, PT-100, NVP-DDP-728, LAF237, etc.), β3 agonists (e.g., CL-316243, SR-58611-A, UL-TG-307, SB-226552, AJ-9677, BMS-196085, AZ-40140 etc.), amylin agonists (e.g., pramlintide etc.), phosphotyrosine phosphatase inhibitors (e.g., sodium vanadate etc.), gluconeogenesis inhibitors (e.g., glycogen phosphorylase inhibitors, glucose-6-phosphatse inhibitors, glucagon antagonists etc.) and SGLUT (sodium-glucose cotransporter) inhibitors (e.g., T-1095 etc.).

Examples of the therapeutic agents for diabetic complications include aldose reductase inhibitors (e.g., tolrestat, epalrestat, zenarestat, zopolrestat, minalrestat, fidarestat (SNK-860), CT-112 etc.), neurotrophic factors (e.g., NGF, NT-3, BDNF etc.), neurotrophin production-secretion promoters [e.g., neurotrophin production-secretion promoters described in WO01/14372 (e.g., 4-(4-chlorophenyl)-2-(2-methyl-1-imidazolyl)-5-(3-(2-methylphenoxy)propyl)oxazole and the like)], PKC inhibitors (e.g., LY-333531 etc.), AGE inhibitors (e.g., ALT946, pimagedine, pyratoxanthine, N-phenacylthiazolium bromide (ALT766), EXO-226 etc.), active oxygen scavengers (e.g., thioctic acid etc.) and cerebral vasodilators (e.g., tiapride, mexiletine etc.).

Examples of the therapeutic agents for hyperlipidemia include HMG-CoA reductase inhibitors (e.g., pravastatin, simvastatin, lovastatin, atorvastatin, fluvastatin, lipantil, cerivastatin, itavastatin, rosuvastatin (ZD-4522), or their salts (e.g., sodium salts, calcium salts, etc.), etc.), fibrate compounds (e.g., bezafibrate, beclofibrate, binifibrate, cyprofibrate, clinofibrate, clofibrate, clofibric acid, etofibrate, fenofibrate, gemfibrozil, nicofibrate, pirifibrate, ronifibrate, simfibrate, theofibrate etc.), squalene synthase inhibitors (e.g., compounds described in WO97/10224 (e.g., 1-[[(3R,5S)-1-(3-acetoxy-2,2-dimethylpropyl)-7-chloro-5-(2,3-dimethoxyphenyl)-2-oxo-1,2,3,5-tetrahydro-4,1-benzooxazepin-3-yl]acetyl]piperidine-4-acetic acid, etc.), ACAT inhibitors (e.g., Avasimibe, Eflucimibe etc.), anion exchange resins (e.g., colestyramine etc.), probucol, nicotinic acid drugs (e.g., nicomol, niceritrol etc.), ethyl icosapentate, plant sterols (e.g., soysterol, γ-oryzanol etc.) and the like.

Examples of the antihypertensive agents include angiotensin converting enzyme inhibitors (e.g., captopril, enalapril, delapril etc.), angiotensin II antagonists (e.g., candesartan cilexetil, losartan, eprosartan, valsartan, telmisartan, irbesartan, tasosartan etc.), calcium antagonists (e.g., manidipine, nifedipine, nicardipine, amlodipine, efonidipine etc.), potassium channel openers (e.g., levcromakalim, L-27152, AL 0671, NIP-121 etc.), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex etc.), pancreatic lipase inhibitors (e.g., orlistat etc.), β3 agonists (e.g., CL-316243, SR-58611-A, UL-TG-307, SB-226552, AJ-9677, BMS-196085, AZ-40140 etc.), peptidic anorexiants (e.g., leptin, CNTF (Ciliary Neurotropic Factor) etc.), cholecystokinin agonists (e.g., lintitript, FPL-15849 etc.) and the like.

Examples of the diuretics include xanthine derivatives (e.g., sodium salicylate and theobromine, calcium salicylate and theobromine etc.), thiazide preparations (e.g., ethiazide, cyclopenthiazide, trichloromethyazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide etc.), chlorobenzenesulfonamide preparations (e.g., chlortalidone, mefruside, indapamide etc.), azosemide, isosorbide, etacrynic acid, piretanide, bumetanide, furosemide and the like.

Examples of the antithrombotic agents include heparin (e.g., heparin sodium, heparin calcium, dalteparin sodium etc.), warfarin (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

The active ingredient is preferably a therapeutic agent for diabetes, more preferably a biguanide, particularly preferably metformin or a salt thereof (preferably metformin hydrochloride).

In addition, as the active ingredient, a therapeutic agent for hyperlipidemia is also preferable. The therapeutic agent for hyperlipidemia is more preferably an HMG-CoA reductase inhibitor. Particularly, simvastatin and the like are preferable.

The amount of the active ingredient in the core of the present invention is, for example, 0.1-100 parts by weight, preferably 1-99 parts by weight, per 100 parts by weight of the core of the present invention.

The core of the present invention is preferably a tablet containing an active ingredient (preferably a therapeutic agent for diabetes, more preferably a biguanide, particularly preferably metformin hydrochloride). The shape of the tablet may be any from round, caplet, oblong and the like. The tablet can be produced by, for example, mixing or granulating the active ingredient with the aforementioned additives, and then compression-molding the obtained mixture or granules after mixing, according to methods conventionally employed in the field of pharmaceutical preparation.

Here, mixing is done using, for example, a mixer such as a V-type mixer, a tumbler mixer and the like, and granulation is done using, for example, a high speed mixer granulator, a fluid bed granulator and the like. For compression-molding, punching is done generally at a pressure of 5-35 kN/cm² using a single punch tableting machine, rotary tableting machine and the like.

When the active ingredient contained in the core of the present invention is not a pharmaceutical agent for a single administration per day (e.g., in the case of a pharmaceutical agent for administration twice or three times a day), the core containing said active ingredient is preferably a sustained release preparation.

When the compatibility of pioglitazone hydrochloride and active ingredient contained in the core of the present invention is poor, the core containing the active ingredient may be coated with the aforementioned coating material and the like.

The core of the present invention is more preferably a sustained release preparation (preferably tablet) containing a biguanide (preferably metformin hydrochloride). As such preparation, for example, a controlled release pharmaceutical agent tablet described in WO99/47125, a two-layer controlled release delivery system described in WO99/47128, a controlled release oral pharmaceutical agent described in U.S. Pat. No. 6,340,475 and the like can be mentioned.

As a sustained release preparation containing a biguanide,
(1) a biguanide-containing tablet coated with a semipermeable membrane coating, which contains cellulose acetate (preferably cellulose acetate having an acetyl content of 39.3-40%), polyethylene glycol (preferably polyethylene glycol 400 and the like) and triacetin (said semipermeable membrane coating may have a hole or pore);
(2) a tablet obtained by mixing a release-sustaining composition containing sodium carboxymethyl cellulose, hydroxypropylmethyl cellulose 2910, hydroxypropylmethyl cellulose 2208 and crystalline cellulose with a biguanide, and then compression-molding the mixture, and the like are preferable.

In the production method of the present invention, the coating is done according to known methods. For example, coating is done using a film coating equipment.

In addition, coating is done such that the core of the present invention is generally 50-99 parts by weight, preferably 70-99 parts by weight, more preferably 70-98 parts by weight, per 100 parts by weight of the obtained coated preparation.

Furthermore, the "preparation coated with pioglitazone hydrochloride" obtained according to the production method of the present invention (hereinafter sometimes to be abbreviated as a coated preparation of the present invention) may be coated with the aim of improving preparation strength, improving a bitter taste, increasing light resistance, coloring and the like of the coated preparation. Such coating can be applied according to a known method and using, for example, the aforementioned coating material and the like.

As the dosage form of the coated preparation of the present invention, for example, tablet, capsule, granule, powder, troche and the like can be mentioned. The dosage form of the coated preparation is preferably a tablet. The shape of the tablet may be any from round, caplet, oblong and the like. In addition, a mark or a letter may be printed on the tablet for identifiability, and a separating line may be made to facilitate division.

The amount of the active ingredient in the coated preparation of the present invention is, for example, generally 0.01-99 parts by weight, preferably 0.1-99 parts by weight, per 100 parts by weight of the coated preparation. Particularly, when the active ingredient is a biguanide (preferably metformin hydrochloride), the amount of the biguanide in the coated preparation is, for example, generally 5-98 parts by weight, preferably 15-96 parts by weight, per 100 parts by weight of the coated preparation.

The amount of pioglitazone hydrochloride in the coated preparation of the present invention is, for example, generally 0.01-30 parts by weight, preferably 0.5-25 parts by weight, more preferably 0.5-10 parts by weight, per 100 parts by weight of the coated preparation.

The coated preparation of the present invention can be administered orally and safely to mammals (e.g., mouse, rat, rabbit, cat, dog, cattle, horse, monkey, human and the like).

The coated preparation of the present invention is superior in the characteristics of the preparation, such as dissolution property (particularly, dissolution property immediately after administration to the body or within 15 min. from the start of a dissolution test) of pioglitazone hydrochloride and the like, and is useful as a prophylactic or therapeutic agent for, for example, diabetes (e.g., type-1 diabetes, type-2 diabetes, gestational diabetes etc.), hyperlipidemia (e.g., hypertriglyceridemia, hypercholesterolemia, hypo-HDL-emia, postprandial hyperlipidemia etc.), impaired glucose tolerance [IGT (Impaired Glucose Tolerance)], diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection etc.), diabetic gangrene, xerostomia, hypacusis, cerebrovascular disorder, peripheral blood circulation disorder etc.], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease etc.), muscular dystrophy, myocardial infarction, angina pectoris, cerebrovascular accident (e.g., cerebral infarction, cerebral apoplexy), insulin resistance syndrome, Syndrome X, hyperinsulinemia, hyperinsulinemia-induced sensory disorder, tumor (e.g., leukemia, breast cancer, prostate cancer, skin cancer etc.), irritable bowel syndrome, acute or chronic diarrhea, inflammatory diseases [e.g., Alzheimer's disease, chronic rheumatoid arthritis, spondylitis deformans, osteoarthritis cleformans, lumbagor pain, gout, postoperative or traumatic inflammation, remission of tumentia, neuralgia, pharyngolaryngitis, cystitis, hepatitis (inclusive of nonalcoholic steatohepatitis), pneumonia, pancreatitis, inflammatory bowel disease, ulcerative colitis, etc.], visceral obesity syndrome, arteriosclerosis (e.g., atherosclerosis etc.) and the like.

The coated preparation of the present invention is also useful for the secondary prevention (e.g., secondary prevention of cardiovascular event such as myocardial infarction etc.) and suppression of progression (e.g., suppression of progression of impaired glucose tolerance into diabetes, suppression of progression of arteriosclerosis in diabetic patients) of the above-mentioned various diseases.

The dose of the coated preparation of the present invention is 7.5-60 mg/day, preferably 15-60 mg/day, more preferably 15-45 mg/day, based on the amount of pioglitazone hydrochloride, for an adult (body weight 60 kg).

When the coated preparation of the present invention is obtained using a core containing an active ingredient, the coated preparation preferably contains an effective amount of the active ingredient. For example, the effective amount when the active ingredient is a biguanide (preferably metformin hydrochloride) is 125-2550 mg/day, preferably 250-2550 mg/day, for an adult (body weight 60 kg). Furthermore, an effective amount when the active ingredient is an HMG-CoA reductase inhibitor (preferably simvastatin, atorvastatin calcium, fluvastatin sodium) is 1-100 mg/day, preferably 5-80 mg/day, per an adult (body weight 60 kg).

The coated preparation of the present invention may be used in combination with one or more pharmaceutical agents selected from therapeutic agents for diabetes, therapeutic agents for diabetic complications, therapeutic agents for hyperlipidemia, antihypertensive agents, antiobesity agents, diuretics, antithrombotic agents and the like (hereinafter sometimes to be abbreviated as a concomitant drug). As such concomitant drugs, those exemplified above as the active ingredient can be used. The time of administration of the coated preparation of the present invention and that of the concomitant drug are not limited, and they may be administered simultaneously or at staggered times to the administration subject. The dose of the concomitant drug can be appropriately determined based on the dose clinically employed. In addition, the mixing ratio of the coated preparation of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the coated preparation.

Use of the concomitant drug in this way provides superior effects such as 1) enhancing the action of the coated preparation of the present invention or the concomitant drug (synergistic effect on the action of the pharmaceutical agents), 2) reducing the dose of the coated preparation of the present invention or the concomitant drug (effect of reducing the dose of pharmaceutical agents as compared to a single drug administration), 3) reducing the secondary action (e.g., body weight gain action, ketosis, acidosis) of the coated preparation of the present invention or the concomitant drug, and the like.

The present invention further relates to "a method for improving dissolution of pioglitazone hydrochloride from a preparation coated with pioglitazone hydrochloride, which comprises, when producing said preparation, coating with an aqueous dispersion of pioglitazone hydrochloride comprising a coating material having a low viscosity".

Use of the production method of the present invention when producing a preparation coated with pioglitazone hydrochloride can afford a coated preparation superior in the dissolution property (particularly, dissolution property immediately after administration to the body or within 15 min. from the start of a dissolution test) of pioglitazone hydrochloride.

The present invention moreover relates to "a coated preparation obtained according to the production method of the present invention, which releases not less than 50% of pioglitazone hydrochloride in 15 minutes in a dissolution test by a rotating basket method using a hydrochloric acid-potassium chloride buffer (pH 2.0) as a test solution at 37° C., 100 rpm". As used herein, the dissolution test is performed according to the method described in The Japanese Pharmacopoeia 14th Edition. The "hydrochloric acid-potassium chloride buffer (pH 2.0)" used as a test solution can be prepared according to a known method. The amount of the hydrochloric acid-potassium chloride buffer used as a test solution is generally 900 mL.

The "coated preparation obtained according to the production method of the present invention, which releases not less than 50% of pioglitazone hydrochloride in 15 minutes in a dissolution test by a rotating basket method using a hydrochloric acid-potassium chloride buffer (pH 2.0) as a test solution at 37° C., 100 rpm" can be administered orally and safely to mammals (e.g., mouse, rat, rabbit, cat, dog, bovine, horse, monkey, human and the like) in the same manner as the aforementioned coated preparation of the present invention, wherein the target disease, dose and the like are the same as those in the aforementioned coated preparation of the present invention.

The present invention moreover relates to "a coated preparation obtained according to the production method of the present invention, which releases not less than 50% of pioglitazone hydrochloride in 15 minutes in a dissolution test by a paddle method using a hydrochloric acid-potassium chloride buffer (pH 2.0) as a test solution at 37° C., 50 rpm". As used herein, the dissolution test is performed according to the method described in The Japanese Pharmacopoeia 14th Edition. The "hydrochloric acid-potassium chloride buffer (pH 2.0)" used as a test solution can be prepared according to a known method. The amount of the hydrochloric acid-potassium chloride buffer used as a test solution is generally 900 mL.

The "coated preparation obtained according to the production method of the present invention, which releases not less than 50% of pioglitazone hydrochloride in 15 minutes in a dissolution test by a paddle method using a hydrochloric acid-potassium chloride buffer (pH 2.0) as a test solution at 37° C., 50 rpm" can be administered orally and safely to mammals (e.g., mouse, rat, rabbit, cat, dog, bovine, horse, monkey, human and the like) in the same manner as the aforementioned coated preparation of the present invention, wherein the target disease, dose and the like are the same as those in the aforementioned coated preparation of the present invention.

The present invention is explained in detail in the following by referring to Examples, Reference Examples, Comparative Examples and Experimental Examples, which are not to be construed as limitative.

As the preparation additives (e.g., D-mannitol, corn starch, hydroxypropyl cellulose, magnesium stearate, microcrystalline cellulose, lactose, hydroxypropyl methylcellulose, polyethylene glycol 6000, titanium oxide, low-substituted hydroxypropyl cellulose, talc, carboxymethylcellulose calcium) used in the following Examples, Reference Examples and Comparative Examples, those capable of meeting the standards of The Japanese Pharmacopoeia 14th Edition were used. As triethyl citrate, yellow ferric oxide, ferric oxide and the aqueous ethylcellulose dispersion, those capable of meeting the standards of Japanese Pharmaceutical Excipients (1998) were used.

EXAMPLE 1

Hydroxypropyl cellulose (26.4 g, Grade SSL, Nippon Soda Co., Ltd.) (viscosity of 5% aqueous solution at 20° C.: 8 mPa·s), polyethylene glycol 6000 (1.32 g), titanium oxide (2.64 g) and pioglitazone hydrochloride (16.5 g) were dispersed in water (297 g) to give a coating solution.

The tablets (300 g) obtained in Reference Example 1 were fed in a film coating equipment (Hicoater-Mini, Freund Industrial Co. Ltd.) and coated with the aforementioned coating solution at an inlet temperature of 70° C. to give a coated preparation weighing 260.9 mg per tablet.

EXAMPLE 2

Hydroxypropyl cellulose (24 g, Grade SL, Nippon Soda Co., Ltd.) (viscosity of 5% aqueous solution at 20° C.: 24 mPa·s), polyethylene glycol 6000 (1.2 g), titanium oxide (2.4 g) and pioglitazone hydrochloride (15 g) were dispersed in water (344.7 g) to give a coating solution.

The tablets (250 g) obtained in Reference Example 2 were fed in a film coating equipment (Hicoater-Mini, Freund Industrial Co. Ltd.) and coated with the aforementioned coating solution at an inlet temperature of 75° C. to give a coated preparation weighing 381 mg per tablet.

EXAMPLE 3

Hydroxypropyl cellulose (24 g, Grade SSL, Nippon Soda Co., Ltd.) (viscosity of 5% aqueous solution at 20° C.: 8 mPa·s), polyethylene glycol 6000 (1.2 g), titanium oxide (2.4 g) and pioglitazone hydrochloride (15 g) were dispersed in water (344.7 g) to give a coating solution.

The tablets (250 g) obtained in Reference Example 2 were fed in a film coating equipment (Hicoater-Mini, Freund Industrial Co. Ltd.) and coated with the aforementioned coating solution at an inlet temperature of 75° C. to give a coated preparation weighing 382 mg per tablet.

EXAMPLE 4

Hydroxypropyl methylcellulose (24 g, Grade MW, Shin-Etsu Chemical Co., Ltd.) (viscosity of 5% aqueous solution at 20° C.: 21 mPa·s), polyethylene glycol 6000 (1.2 g), titanium oxide (2.4 g) and pioglitazone hydrochloride (15 g) were dispersed in water (310 g) to give a coating solution.

The tablets (250 g) obtained in Reference Example 2 were fed in a film coating equipment (Hicoater-Mini, Freund Industrial Co. Ltd.) and coated with the aforementioned coating solution at an inlet temperature of 70° C. to give a coated preparation weighing 382 mg per tablet.

EXAMPLE 5

Hydroxypropyl methylcellulose (24 g, Grade EW, Shin-Etsu Chemical Co., Ltd.) (viscosity of 5% aqueous solution at 20° C.: 12 mPa·s), polyethylene glycol 6000 (1.2 g), titanium oxide (2.4 g) and pioglitazone hydrochloride (15 g) were dispersed in water (344.7 g) to give a coating solution.

The tablets (250 g) obtained in Reference Example 2 were fed in a film coating equipment (Hicoater-Mini, Freund Industrial Co. Ltd.) and coated with the aforementioned coating solution at an inlet temperature of 70° C. to give a coated preparation weighing 382 mg per tablet.

EXAMPLE 6

Polyvinyl alcohol-polyethylene glycol graft copolymer (trademark: Kollicoat IR, 24 g, BASF, Germany) (viscosity of 5% aqueous solution at 20° C.: 18 mPa·s), titanium oxide (2.4 g) and pioglitazone hydrochloride (15 g) were dispersed in water (200 g) to give a coating solution.

The tablets (250 g) obtained in Reference Example 2 were fed in a film coating equipment (Hicoater-Mini, Freund Industrial Co. Ltd.) and coated with the aforementioned coating solution at an inlet temperature of 75° C. to give a coated preparation weighing 380.5 mg per tablet.

EXAMPLE 7

Hydroxypropyl cellulose (48.0 g, Grade SL, Nippon Soda Co., Ltd.) (viscosity of 5% aqueous solution at 20° C.: 24 mPa·s), polyethylene glycol 6000 (2.4 g), titanium oxide (4.8 g) and pioglitazone hydrochloride (30.0 g) were dispersed in water (540 g) to give a coating solution.

The tablets (250 g) obtained in Reference Example 4 were fed in a film coating equipment (Hicoater-Mini, Freund Industrial Co. Ltd.) and coated with the aforementioned coating solution at an inlet temperature of 90° C. to give a coated preparation weighing 459 mg per tablet.

EXAMPLE 8

Polyvinyl alcohol-polyethylene glycol graft copolymer (trademark: Kollicoat IR, 48.0 g, BASF, Germany) (viscosity of 5% aqueous solution at 20° C.: 18 mPa·s), polyethylene glycol 6000 (2.4 g), titanium oxide (4.8 g) and pioglitazone hydrochloride (30.0 g) were dispersed in water (540 g) to give a coating solution.

The tablets (250 g) obtained in Reference Example 4 were fed in a film coating equipment (Hicoater-Mini, Freund Industrial Co. Ltd.) and coated with the aforementioned coating solution at an inlet temperature of 90° C. to give a coated preparation weighing 461 mg per tablet.

EXAMPLE 9

Polyvinyl alcohol-polyethylene glycol graft copolymer (trademark: Kollicoat IR, 18.0 g, BASF, Germany) (viscosity of 5% aqueous solution at 20° C.: 18 mPa·s), titanium oxide (1.8 g), low-substituted hydroxypropyl cellulose (trademark: L-HPC 31, 3.6 g, Shin-Etsu Chemical Co., Ltd.) and pioglitazone hydrochloride (11.3 g) were dispersed in water (207 g) to give a coating solution.

The tablets (30 tablets) obtained in Reference Example 5 and the tablets (240 g, about 800 tablets) obtained in Reference Example 3 were fed in a film coating equipment (Hicoater-Mini, Freund Industrial Co. Ltd.) and coated with the aforementioned coating solution at an inlet temperature of 95° C. From the appearance of the obtained tablets, coated preparations (479 mg per tablet) containing the tablet obtained in Reference Example 5 as a core were selected.

EXAMPLE 10

Hydroxypropyl cellulose (24.0 g, Grade SSL, Nippon Soda Co., Ltd.) (viscosity of 5% aqueous solution at 20° C.: 8 mPa·s), polyethylene glycol 6000 (1.2 g), titanium oxide (2.4 g) and pioglitazone hydrochloride (15.0 g) were dispersed in water (350 g) to give a coating solution.

Glucophage XR tablets (trademark, 30 tablets, sustained release tablet containing 500 mg of metformin hydrochloride)(Bristol-Myers Squibb Company) and the tablets (250 g) obtained in Reference Example 3 were fed in a film coating equipment (Hicoater-Mini, Freund Industrial Co. Ltd.) and coated with the aforementioned coating solution at an inlet temperature of 70° C. From the appearance of the obtained tablets, coated preparations (weight per tablet: 1.086 g) containing the Glucophage XR tablet as a core and containing metformin hydrochloride 500 mg/pioglitazone hydrochloride 16.53 mg per tablet were selected.

EXAMPLE 11

Polyvinyl alcohol-polyethylene glycol graft copolymer (trademark: Kollicoat IR, 36.0 g, BASF, Germany) (viscosity of 5% aqueous solution at 20° C.: 18 mPa·s), titanium oxide (3.6 g) and pioglitazone hydrochloride (22.5 g) were dispersed in water (300 g) to give a coating solution.

Glucophage XR tablets (trademark, 30 tablets, sustained release tablet containing 500 mg of metformin hydrochloride)(manufactured by Bristol-Myers Squibb Company) and the tablets (250 g) obtained in Reference Example 3 were fed in a film coating equipment (Hicoater-Mini, Freund Industrial Co. Ltd.) and coated with the aforementioned coating solution at an inlet temperature of 70° C. From the appearance of the obtained tablets, coated preparations (weight per tablet: 1.082 g) containing the Glucophage XR tablet as a core and containing metformin hydrochloride 500 mg/pioglitazone hydrochloride 16.53 mg per tablet were obtained.

EXAMPLE 12

Hydroxypropyl cellulose (24.0 g, Grade SL, Nippon Soda Co., Ltd.) (viscosity of 5% aqueous solution at 20° C.: 24 mPa·s), polyethylene glycol 6000 (1.2 g), titanium oxide (2.4 g) and pioglitazone hydrochloride (15.0 g) were dispersed in water (350 g) to give a coating solution.

Lipovas tablet 20 (trademark, 30 tablets, Banyu Pharmaceutical Co., Ltd., major axis 14.0 mm, minor axis 7.5 mm, weight 400 mg) containing simvastatin as an active ingredient and the tablets (250 g) obtained in Reference Example 9 were fed in a film coating equipment (Hicoater-Mini, Freund Industrial Co. Ltd.) and coated with the aforementioned coating solution at an inlet temperature of 70° C. From the appearance of the obtained tablets, coated preparations (weight per tablet: 449 mg) containing simvastatin 20 mg/pioglitazone hydrochloride 17.78 mg per tablet were obtained.

EXAMPLE 13

Hydroxypropyl cellulose (72 g, Grade SL, Nippon Soda Co., Ltd.) (viscosity of 5% aqueous solution at 20° C.: 24 mPa·s), polyethylene glycol 6000 (3.6 g), titanium oxide (7.2 g) and pioglitazone hydrochloride (45 g) were dispersed in water (1050 g) to give a coating solution.

The tablets (30 tablets) obtained in Reference Example 10 and the tablets (250 g) obtained in Reference Example 9 were fed in a film coating equipment (Hicoater-Mini, Freund Industrial Co. Ltd.) and coated with the aforementioned coating solution at an inlet temperature of 80° C. From the appearance of the obtained tablets, coated preparations (weight per tablet: 349 mg) containing simvastatin 15 mg/pioglitazone hydrochloride 16.25 mg per tablet were obtained.

EXAMPLE 14

Hydroxypropyl cellulose (72 g, Grade SL, Nippon Soda Co., Ltd.) (viscosity of 5% aqueous solution at 20° C.: 24 mPa·s), polyethylene glycol 6000 (3.6 g), titanium oxide (7.2 g) and pioglitazone hydrochloride (45 g) were dispersed in water (1050 g) to give a coating solution.

The tablets (30 tablets) obtained in Reference Example 11 and the tablets (250 g) obtained in Reference Example 9 were fed in a film coating equipment (Hicoater-Mini, Freund Industrial Co. Ltd.) and coated with the aforementioned coating solution at an inlet temperature of 80° C. From the appearance of the obtained tablets, coated preparations (weight per tablet: 349 mg) containing atorvastatin calcium 21 mg/pioglitazone hydrochloride 16.93 mg per tablet were obtained.

REFERENCE EXAMPLE 1

D-mannitol (2176 g) and corn starch (918 g) were charged in a fluid bed granulator (FD-3S, manufactured by POWREX CORPORATION) and granulated while spraying an aqueous solution (1700 g) containing hydroxypropyl cellulose (102 g), which was followed by a drying step to give granules. Microcrystalline cellulose (160.2 g) and magnesium stearate (32 g) were added to the obtained granule powder (3012 g) and mixed. The obtained granule powder mixture was tableted by a tableting machine (Correct 19K, manufactured by Kikusui Seisakusho Ltd.) (tablet size: 8.5 mmφ, compression pressure 9 KN/punch) to give tablets weighing 244 mg per tablet.

REFERENCE EXAMPLE 2

Lactose (2470 g), corn starch (315 g) and carmellose calcium (157.5 g) were charged in a fluid bed granulator (FD-3S, manufactured by POWREX CORPORATION) and granulated while spraying an aqueous solution (1575 g) containing hydroxypropyl cellulose (94.5 g), which was followed by a drying step to give granules. Carmellose calcium (89.3 g) and magnesium stearate (17.9 g) were added to the obtained granule powder (2868 g) and mixed. The obtained granule powder mixture was tableted by a tableting machine (Correct 19K, manufactured by Kikusui Seisakusho Ltd.)(tablet size: major axis 12 mm, minor axis 7 mm, compression pressure 15 KN/punch) to give tablets weighing 350 mg per tablet.

REFERENCE EXAMPLE 3

Lactose (1976 g), corn starch (252 g) and carboxymethylcellulose calcium (126 g) were charged in a fluid bed granulator (FD-3S, manufactured by POWREX CORPORATION) and granulated while spraying an aqueous solution (1260 g) containing hydroxypropyl cellulose (75.6 g), which was followed by a drying step to give granules. Carboxymethylcellulose calcium (71.4 g) and magnesium stearate (14.3 g) were added to the obtained granule powder (2294 g) and mixed. The obtained granule powder mixture was tableted by a tableting machine (Correct 19K, manufactured by Kikusui Seisakusho Ltd.) (tablet size: 9 mmφ, compression pressure 7 KN/punch) to give tablets weighing 300 mg per tablet.

REFERENCE EXAMPLE 4

The tablets (400 g) obtained in Reference Example 2 were fed in a film coating equipment (Hicoater-Mini, Freund Industrial Co. Ltd.), coated with a coating solution containing aqueous ethylcellulose dispersion (trademark: Aquacoat, Asahi Kasei Corporation, 148.2 g), talc (2.2 g), triethyl citrate (13.3 g), yellow ferric oxide (0.36 g) and water (231.1 g) at an inlet temperature of 90° C., whereby tablets weighing 391 mg per tablet were obtained. Furthermore, the tablets were coated with a solution of hydroxypropyl methylcellulose (47.3 g), polyethylene glycol 6000 (9.5 g), titanium oxide (6.3 g) and ferric oxide (0.09 g) in water (473 g) under the similar conditions as above to give tablets weighing 416 mg per tablet.

REFERENCE EXAMPLE 5

The tablets (400 g) obtained in Reference Example 2 were fed in a film coating equipment (Hicoater-Mini, Freund Industrial Co. Ltd.), coated with a coating solution containing aqueous ethylcellulose dispersion (trademark: Aquacoat, Asahi Kasei Corporation, 74.1 g), talc (1.1 g), triethyl citrate (6.7 g), yellow ferric oxide (0.18 g) and water (115.6 g) at an inlet temperature of 58° C., whereby tablets weighing 381 mg per tablet were obtained. Furthermore, the tablets were coated with a solution of hydroxypropyl methylcellulose (47.3 g), polyethylene glycol 6000 (9.5 g), titanium oxide (6.3 g) and ferric oxide (0.09 g) in water (473 g) under the similar conditions as above to give tablets weighing 429 mg per tablet.

REFERENCE EXAMPLE 6

Hydroxypropyl cellulose (26.4 g, Grade L, Nippon Soda Co., Ltd.) (viscosity of 5% aqueous solution at 20° C.: 42 mPa·s), polyethylene glycol 6000 (1.32 g), titanium oxide (2.64 g) and pioglitazone hydrochloride (16.5 g) were dispersed in water (297 g) to give a coating solution.
The tablets (300 g) obtained in Reference Example 1 were fed in a film coating equipment (Hicoater-Mini, Freund Industrial Co. Ltd.) and coated with the aforementioned coating solution at an inlet temperature of 70° C. to give a coated preparation weighing 262.1 mg per tablet.

REFERENCE EXAMPLE 7

Hydroxypropyl cellulose (24 g, Grade L, Nippon Soda Co., Ltd.) (viscosity of 5% aqueous solution at 20° C.: 42 mPa·s), polyethylene glycol 6000 (1.2 g), titanium oxide (2.4 g) and pioglitazone hydrochloride (15 g) were dispersed in water (344.7 g) to give a coating solution.
The tablets (250 g) obtained in Reference Example 2 were fed in a film coating equipment (Hicoater-Mini, Freund Industrial Co. Ltd.) and coated with the aforementioned coating solution at an inlet temperature of 75° C. to give a coated preparation weighing 382 mg per tablet.

REFERENCE EXAMPLE 8

Hydroxypropyl methylcellulose (24 g, Grade R, Shin-Etsu Chemical Co., Ltd.) (viscosity of 5% aqueous solution at 20° C.: 40 mPa·s), polyethylene glycol 6000 (1.2 g), titanium oxide (2.4 g) and pioglitazone hydrochloride (15 g) were dispersed in water (270 g) to give a coating solution.
The tablets (250 g) obtained in Reference Example 2 were fed in a film coating equipment (Hicoater-Mini, Freund Industrial Co. Ltd.) and coated with the aforementioned coating solution at an inlet temperature of 70° C. to give a coated preparation weighing 381.2 mg per tablet.

REFERENCE EXAMPLE 9

Lactose (41160 g), corn starch (5250 g) and carmellose calcium (2625 g) were charged in a fluid bed granulator (FD-WSG-60, POWREX CORPORATION) and granulated while spraying an aqueous solution (31510 g) containing hydroxypropyl cellulose (1575 g), which was followed by a drying step to give granules. Carmellose calcium (1491 g) and magnesium stearate (298.2 g) were added to the obtained granule powder (47910 g) and mixed. The obtained granule powder mixture was tableted by a tableting machine (Correct 19K, Kikusui Seisakusho Ltd.) (tablet size: 7 mmφ, compression pressure 5.7 KN/punch) to give tablets weighing 105 mg per tablet.

REFERENCE EXAMPLE 10

Lipovas tablets 5 mg (trademark, Banyu Pharmaceutical Co., Ltd., weight 100 mg) containing simvastatin as an active ingredient were pulverized in a mortar, and 300 mg of the pulverized powder corresponding to 15 mg of simvastatin was tableted by a universal testing instrument (Shimadzu Corporation, UH-10A) (compression pressure 9.5 KN/punch) using a 9.0 mmφ punch with a R and a die to give 30 tablets.

REFERENCE EXAMPLE 11

Lipitor tablets 5 mg (trademark, Yamanouchi Pharmaceutical Co., Ltd., weight about 72 mg) containing atorvastatin calcium as an active ingredient were pulverized in a mortar, and 300 mg of the pulverized powder corresponding to 21 mg of atorvastatin calcium was tableted by a universal testing instrument (Shimadzu Corporation, UH-10A, compression pressure 9.5 KN/punch) using a 9.0 mmφ punch with a R and a die to give 30 tablets.

COMPARATIVE EXAMPLE 1

Hydroxypropyl cellulose (48.0 g, Grade L, Nippon Soda Co., Ltd.) (viscosity of 5% aqueous solution at 20° C.: 42 mPa·s), polyethylene glycol 6000 (2.4 g), titanium oxide (4.8 g) and pioglitazone hydrochloride (30.0 g) were dispersed in water (540 g) to give a coating solution.

The tablets (250 g) obtained in Reference Example 4 were fed in a film coating equipment (Hicoater-Mini, Freund Industrial Co. Ltd.) and coated with the aforementioned coating solution at an inlet temperature of 90° C. to give a coated preparation weighing 459 mg per tablet.

COMPARATIVE EXAMPLE 2

Hydroxypropyl cellulose (48.0 g, Grade L, Nippon Soda Co., Ltd.) (viscosity of 5% aqueous solution at 20° C.: 42 mPa·s), polyethylene glycol 6000 (2.4 g), titanium oxide (4.8 g) and pioglitazone hydrochloride (30.0 g) were dispersed in water (700 g) to give a coating solution.

Lipovas tablet 20 (trademark, 30 tablets, Banyu Pharmaceutical Co., Ltd., major axis 14.0 mm, minor axis 7.5 mm, weight 400 mg) containing simvastatin as an active ingredient and the tablets (250 g) obtained in Reference Example 9 were fed in a film coating equipment (Hicoater-Mini, Freund Industrial Co. Ltd.) and coated with the aforementioned coating solution at an inlet temperature of 70° C. From the appearance of the obtained tablets, coated preparations (weight per tablet: 445 mg) containing simvastatin 20 mg/pioglitazone hydrochloride 16.23 mg per tablet were obtained.

EXPERIMENTAL EXAMPLE 1

The coated preparations obtained in the aforementioned Examples were evaluated for the dissolution property of pioglitazone hydrochloride by a rotating basket method (100 rpm) using a 0.3 M hydrochloric acid-potassium chloride buffer (900 mL, 37° C., pH 2.0). The results are shown in Table 1.

TABLE 1

Dissolution profiles (%) of pioglitazone hydrochloride

| | Time | | | |
|---|---|---|---|---|
| | 15 min. | 30 min. | 45 min. | 60 min. |
| Example 10 | 60.6 | 77.4 | 84.3 | 88.3 |
| Example 11 | 71.2 | 78.1 | 84.7 | 86.9 |

As shown in Table 1, the coated preparation obtained by the production method of the present invention showed superior dissolution property of pioglitazone hydrochloride.

EXPERIMENTAL EXAMPLE 2

The coated preparations obtained in the aforementioned Examples and Comparative Example were evaluated for the dissolution property of pioglitazone hydrochloride by a paddle method (50 rpm) using a 0.3 M hydrochloric acid-potassium chloride buffer (900 mL, 37° C., pH 2.0). The results are shown in Table 2.

TABLE 2

Dissolution profiles (%) of pioglitazone hydrochloride

| | Time | | | |
|---|---|---|---|---|
| | 15 min. | 30 min. | 45 min. | 60 min. |
| Example 7 | 62.0 | 76.5 | 83.5 | 86.2 |
| Example 8 | 80.6 | 89.4 | 91.5 | 91.5 |
| Comparative Example 1 | 29.9 | 44.2 | 55.8 | 65.3 |

As shown in Table 2, the coated preparations of the present invention showed superior dissolution property of pioglitazone hydrochloride.

EXPERIMENTAL EXAMPLE 3

The coated preparations obtained in the aforementioned Example and Comparative Example were evaluated for the dissolution property of pioglitazone hydrochloride in a manner similar to Experimental Example 2. The results are shown in Table 3.

TABLE 3

Dissolution profiles (%) of pioglitazone hydrochloride

| | Time | | | |
|---|---|---|---|---|
| | 15 min. | 30 min. | 45 min. | 60 min. |
| Example 12 | 66.2 | 92.5 | 97.9 | 98.8 |
| Comparative Example 2 | 33.8 | 68.6 | 83.2 | 90.6 |

As shown in Table 3, the coated preparations of the present invention showed superior dissolution property of pioglitazone hydrochloride.

INDUSTRIAL APPLICABILITY

The coated preparation obtained by the production method of the present invention is useful as a therapeutic agent for diabetes and the like and superior in the characteristics of the preparation such as dissolution property (particularly, dissolution property immediately after administration to the body or within 15 minutes from the start of a dissolution test) of pioglitazone hydrochloride and the like and preservation stability.

Moreover, according to the production method of the present invention, preparations coated with pioglitazone hydrochloride can be conveniently produced. Therefore, the production method of the present invention is useful as an industrial production method for the mass production of the aforementioned coated preparation.

The invention claimed is:

1. A method of producing a coated preparation, which method comprises coating a core with an aqueous dispersion, comprising pioglitazone hydrochloride and a core-coating material selected from the group consisting of
   (a) hydroxypropyl cellulose, wherein (i) a 5%(w/v) aqueous solution of which cellulose has a viscosity of 24 mPa·s at 20° C. and/or (ii) a 2%(w/v) aqueous solution of which cellulose has a viscosity of 3.0-5.9 mPa·s at 20° C.;
   (b) hydroxypropyl cellulose, wherein (i) a 5%(w/v) aqueous solution of which cellulose has a viscosity of 8 mPa·s at 20° C. and/or (ii) a 2%(w/v) aqueous solution of which cellulose has a viscosity of 2.0-2.9 mPa·s at 20° C.; and (c) polyvinyl alcohol-polyethylene glycol graft copolymer whose 5%(w/v) aqueous solution has a viscosity of not more than 35 mPa·s at 20° C., wherein the core comprises an active ingredient.

2. The method of claim 1, wherein the active ingredient is a therapeutic agent for diabetes.

3. The method of claim 2, wherein the therapeutic agent for diabetes is a biguanide.

4. The method of claim 3, wherein the biguanide is metformin hydrochloride.

5. The method of claim 1, wherein the active ingredient is a therapeutic agent for hyperlipidemia.

6. The method of claim 5, wherein the therapeutic agent for hyperlipidemia is an HMG-CoA reductase inhibitor.

7. A method for improving dissolution of pioglitazone hydrochloride from a preparation comprising a core coated with pioglitazone hydrochloride, which method comprises, when producing said preparation:

coating the core with an aqueous dispersion, comprising pioglitazone hydrochloride and a core-coating material selected from the group consisting of
  (a) hydroxypropyl cellulose, wherein (i) a 5%(w/v) aqueous solution of which cellulose has a viscosity of 24 mPa·s at 20° C. and/or (ii) a 2%(w/v) aqueous solution of which cellulose has a viscosity of 3.0-5.9 mPa·s at 20° C.;
  (b) hydroxypropyl cellulose, wherein (i) a 5%(w/v) aqueous solution of which cellulose has a viscosity of 8 mPa·s at 20° C. and/or (ii) a 2%(w/v) aqueous solution of which cellulose has a viscosity of 2.0-2.9 mPa·s at 20° C.; and
  (c) polyvinyl alcohol-polyethylene glycol graft copolymer whose 5%(w/v) aqueous solution has a viscosity of not more than 35 mPa·s at 20° C.

8. The method of claim 1, wherein the core is a sustained release preparation containing a biguanide.

9. The method of claim 8, wherein the biguanide is metformin hydrochloride.

10. The method of claim 1, wherein the core is a tablet.

* * * * *

UNITED STATES PATENT AND TRADEMARK OFFICE
CERTIFICATE OF CORRECTION

| | |
|---|---|
| PATENT NO. | : 7,976,853 B2 |
| APPLICATION NO. | : 10/542997 |
| DATED | : July 12, 2011 |
| INVENTOR(S) | : Ohkouchi et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1012 days.

Signed and Sealed this
Eleventh Day of December, 2012

David J. Kappos
*Director of the United States Patent and Trademark Office*